United States Patent [19]
Snyders

[11] Patent Number: 5,169,381
[45] Date of Patent: Dec. 8, 1992

[54] VENTRICULAR ASSIST DEVICE

[76] Inventor: Robert V. Snyders, 31 West Brentmoor, Clayton, Mo. 63105

[21] Appl. No.: 677,520

[22] Filed: Mar. 29, 1991

[51] Int. Cl.$^5$ ................................ A61M 1/12
[52] U.S. Cl. .......................... 600/16; 128/64
[58] Field of Search ........... 128/64; 600/16, 17, 600/18, 37; 623/3

[56] References Cited

U.S. PATENT DOCUMENTS

| | | | |
|---|---|---|---|
| 2,826,193 | 3/1958 | Vineberg | 128/64 |
| 3,371,662 | 3/1968 | Heid et al. | 128/64 |
| 3,985,123 | 10/1976 | Herzlinger et al. | 600/17 |
| 4,536,893 | 8/1985 | Parravicini | 623/3 |
| 4,690,134 | 9/1987 | Snyders | 128/64 |
| 4,957,477 | 9/1990 | Lundbäck | 600/16 |

FOREIGN PATENT DOCUMENTS 0200117 8/1963 U.S.S.R. ................ 128/64

Primary Examiner—Kyle L. Howell
Assistant Examiner—Kennedy J. Schaetzle
Attorney, Agent, or Firm—Polster, Lieder, Woodruff & Lucchesi

[57] ABSTRACT

A ventricular assist device for documenting compressive forces on the right and left ventricular surface of a heart in terms of pressure reactions transmitted from fluid contents in sacs adjacent to these ventricular surfaces to apparatus for displaying the reactions, and a method of monitoring these pressure forces and their effects on the ventricular surfaces for circulating the blood from the ventricular blood pools into the right and left arterial systems.

6 Claims, 1 Drawing Sheet

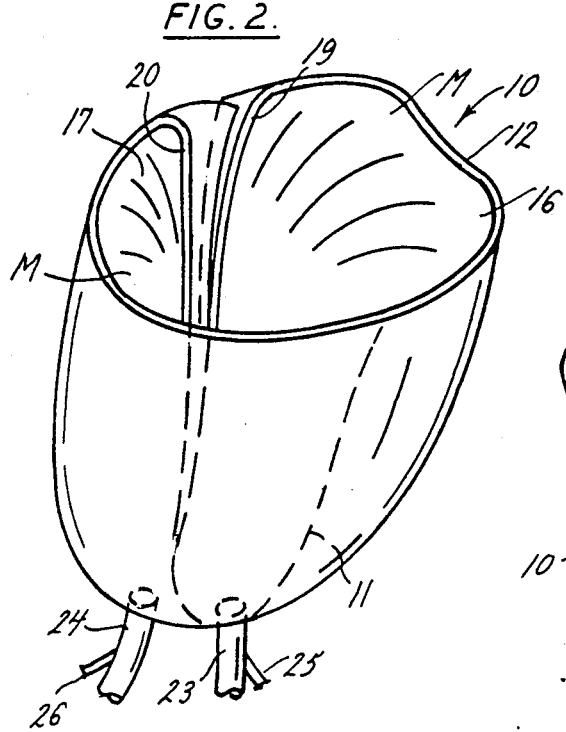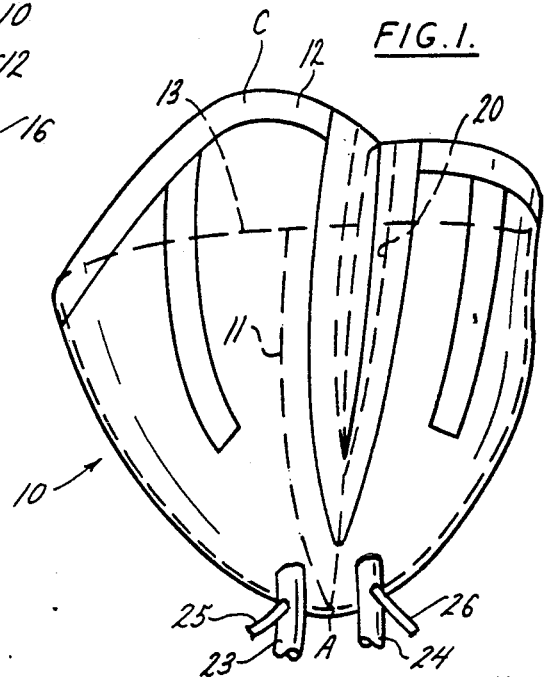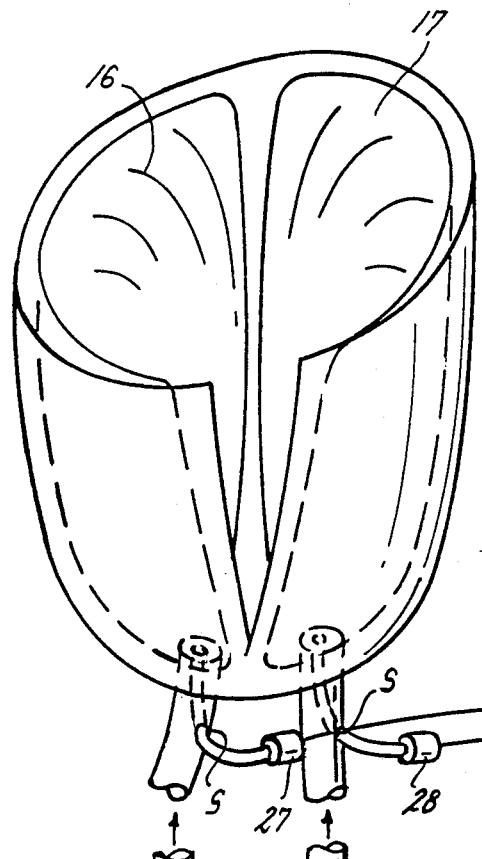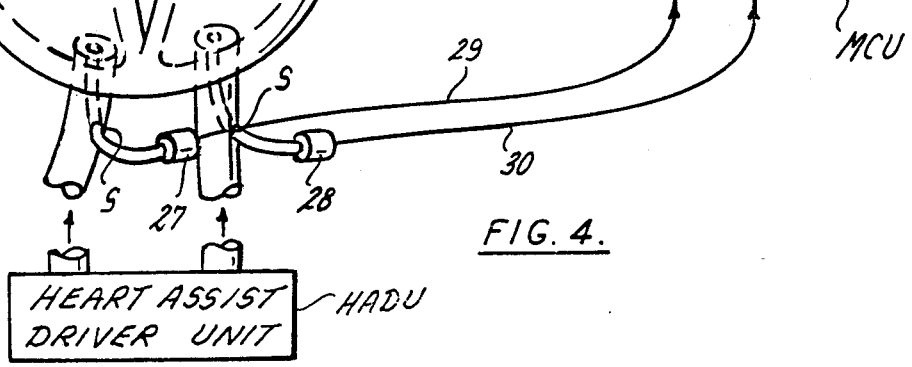

VENTRICULAR ASSIST DEVICE

BACKGROUND OF THE INVENTION

1. Field of the Invention

This invention is particularly concerned with ventricular assist devices for supplementing the cardiac output in a failing heart in sinus rhythm or for effecting increased cardiac output in the dysrhythmic heart, as well as in the event of total arrest or ventricular fibrillation.

2. Description of the Prior Art

It is known that the device of my prior U.S. Pat. No. 4,690,134 of Sep. 1, 1987 has been proposed to fit a human heart to apply a rhythmic pulsating pressure to keep the heart pumping for maintaining a supply of blood at the needed pressure to effect circulation. Somewhat similar devices have been disclosed by Vineberg in U.S. Pat. No. 2,826,193 of Mar. 11, 1958, by Snyders in U.S. Pat. No. 4,690,134 of Sep. 1, 1987, by Parravicini in U.S. Pat. No. 4,536,893, and in the U.S. Pat. No. 3,034,501 of Hewson of May 15, 1962 for an inflatable heart massager in the form of a flexible distendable resilient bag with inner and outer walls of differing thickness, with the outer wall being thicker to minimize relative distending of this wall. It is also disclosed in Hewson that the interior of the bag can be divided into two chambers so each can have its own supply of pressure fluid.

BRIEF DESCRIPTION OF THE INVENTION

An important object of the present invention is to provide a long term ventricular assist functioning device and not simply an acute resuscitation device for the arrested heart such as a device whose primary use would be for cardiomypathic heart dysfunction, and at the same time to provide a substantially totally inert biological device so that rejection problems or other inflammatory response is negated.

Another important object of the present invention is to provide a device that is substantially totally non-interfering relative to ongoing cardiac functions since it may be inserted around the heart and left with no activation should the heart be able to continue its normal function.

The objects of the present invention are achieved by the provision of a ventricular assist device to be inserted through a window cut in the pericardial sac which surrounds a human heart, so that the device receives the heart and is adapted to allow for size adjusting by having a wedge opening to be in substantial alignment with the anterior descending coronary artery so that membranous elastic internal linings of the device are presented to the right and left ventricular surfaces, such membranous linings defining separate right and left ventricular cavitation spaces or chambers which can be charged with a surge of compressed fluid in proper timed relation with the near termination of each normal ventricular beat which will result in increased ventricular ejection volumes per beat according to controlled fluid flow rates and pressures from a master console, as well as result in monitoring the muscular response of the heart.

BRIEF DESCRIPTION OF THE DRAWINGS

The present ventricular assist device is depicted in the accompanying drawings wherein:

FIG. 1 is a side elevational view showing the configuration of the present ventricular assist device;

FIG. 2 is a perspective representation of the present device seen from the posterior view;

FIG. 3 is a transverse sectional view of the present device after being slipped up on the heart so as to show the working relationship of the membranous linings to the ventricular surfaces of the heart; and FIG. 4 is generally schematic view of the system for monitoring the pressure in the sacs of the ventricular assist device in association with heart driver and monitoring apparatus.

DETAILED DESCRIPTION OF THE EMBODIMENT

The ventricular assist device is best seen in FIGS. 1, 2 and 3, and comprises a one-piece shell 10 formed of a flexible but substantially inelastic medical grade elastomer. The shell 10 is given a shape that is characteristic of the ventricular surfaces of a heart, such as a human heart. The interior of the shell is provided with a liner of a thin highly flexible biomedical elastomer to be referred to presently.

The present device, seen in FIGS. 1 and 2, is formed with an upper rim or margin having an anterior superior extremity 12 which extends around the rear which is delineated by an inferior aspect 13 of the posterior rim or margin, the latter being generally opposite, but lower than the anterior superior marginal extremity 12. In one example of an average human heart, the dimension from the apex A to the anterior superior extremity is about 12 cm, the dimension from the apex A to the posterior superior aspect 13 is about 8 cm, the lateral sides about 9 cm, and the transverse dimension through a heart is about 8 cm. Of course, these dimensions will vary depending on the age and the gender of the individual. Also, the shell exterior must be somewhat larger than the extant heart size, about 2 cm for all the given dimensions.

Turning now to FIG. 2 and 3, the shell 10 is provided with a thin, highly flexible and elastic biomedical elastomer membrane means M which is attached and sealed to the interior of the shell. This sealed arrangement effectively encloses the respective chambers 14 and 15 such that any change in the volume of the chambers 14 and 15 is achieved by the elastic flexing of the walls 16 and 17. As shown, shell 10 is formed with a wedge shaped opening or interruption 18 having convergent margins 19 and 20 which extend downwardly toward the apex A of the shell. The wedge opening may extend vertically along the anterior laterial ¾ of the external dimension of the shell and the membranous means M is sealed to the margins 19 and 20.

The view of FIG. 3 illustrates the position of the heart when received in the shell 10. The muscle mass of the heart is indicated at HRV surrounding the right ventricular cavity 21 and at HLV for its left ventricular cavity 22. As the shell 10 is slipped up under the heart, its mass displaces the membranous walls 16 and 17 outwardly so as to decrease the volume of chambers 14 and 15. When the correct size shell 10 is selected, the walls 16 and 17 do not make contact with the interior surface of the shell 10, thereby leaving a space for the introduction of a fluid which acts on just the ventricular surfaces in the predetermined rhythm which assists the normal heart function. Such fluid is communicated with the respective chambers by flexible tubes 23 and 24 which enter the chambers inferiorly. These lines are connected to a well known type of heart driver unit indicated at HDU.

The improvement in the aforementioned functional V.A.D. (Ventricular Assist Device) is the addition of separate right and left sac pressure monitoring lines 25 and 26 connected to each respective sac space behind the walls 16 and 17 of the V.A.D. device. These monitor lines 25 and 26 will be of 90 to 100 mil. tubular conduit caliber, made of any reasonably flexible biocompatible material and each of the lines will traverse internally through the larger gas shuttle lines 23 and 24 entering at a point beyond their separte pressure modulation control sites. The pressure lines 23 and 24 and their differential pressure modulation have been disclosed in my U.S. Pat. No. 4,690,134.

The monitor lines 25 and 26 will access the gas drive lines 23 and 24 via a sealed entry point S and traverse lines 23 and 24 up to their terminus at the point of sac entry. Each monitor line will at its external (proximal) end be fitted with pressure transducers 27 and 28 which covert the pressure response into electrical signals which are conducted by leads 29 and 30 into the electronics of a multi-channel monitoring unit MCU of known character (such as Hewlett-Packard) which provides immediate digital readouts and/or graphic display of ongoing pressures within each sac space. Such readings are essential for documentation of the right and the left epicardial sac pressures needed for appropriate transmural gradients necessary for ejection of ventricular blood pools into the right (pulmonic) and left (systemic) arterial circulation.

Such documentation, though not altering device function, fabrication, or application in any way, nonetheless offers to both the researcher and the clinical user an immediate evidencing of sac pressure values, the characterization of which will be critical to the evaluation of ongoing device integrity and function.

The foregoing VAD is a valuable tool for research applications or for clinical use where the patient can be observed for responsiveness to blood circulation, and most importantly to the response in relation to the pressure in the respective sacs 16 and 17. By locating the transducers 27 and 28 as close as possible to the sacs 16 and 17, the pressure readings can be substantially the equal of the actual pressure in the sacs.

It is considered to be important in the clinical use of the VAD to implant the same as early as possible to avoid heart muscle deterioration. It may appear that the patient is recovering during the early postoperative period depending on hemodynamic evidence that recovery is present and that it can be sustained. Recovery can be determined by reducing the fluid flow from Heart Drive Unit (HDU) and observing the result of the patients heart to assume an increase in the workload without significant elevation of left atrial or pulmonary wedge pressures. Therefor, the immediate knowledge of the pressure needs in the sacs 16 and 17 provides the necessary clue to the condition of patient recovery.

The foregoing disclosure offers documentation to either the researcher or the clinical user immediate evidence of right and left sac pressure values, the characterization of which will be critical to the evaluation of ongoing integrity and function of the VAD.

It is observed in FIG. 1 that the shell 10 is provided with an upper collar C which may be formed of Dacron Silastic material for suturing purposes. A further refinement of the collar can be obtained by extending a free upper Dacron collar flap (not shown) which would enable the higher placement of stabilizing sutures internal to the pericardiam.

Such a higher placement of endo-pericardial sutures would reduce the possibility of cardiac "escape" or upward ejection at the time of sac wall compression (in late systole ideally, or—at other times in the cardiac cycle). This is because there would now be a lesser pericardial width between the endo-pericardial sutures and the Dacron collar suture sites. These pericardial attachments are the ultimate points of fixation to the upper heart structure and great vessels and thus serve to reduce any tendency for cardiac mass "escape" or ejection with device activation and resultant ventricular wall compression. The fact of the heart having an inverted conical shape would generally result in its upward movement when the device is activated. The inertial mass of the heart itself, however, would mitigate against such movement, especially if the compressive wall forces are of brief (30-50 Msec) duration.

The foregoing disclosure offers documentation to either the researcher or the clinical user immediate evidence of right and left sac pressure values, the characterization of which will be critical to the evaluation of ongoing integrity and function of the VAD.

The foregoing disclosure has set forth a preferred embodiment of the invention, but it is to be understood that modifications can be made by those skilled in this art without departing from the scope of the disclosure.

What is claimed is:

1. In a ventricular assist device to enclose the right and left ventricular surfaces of a heart in a shell having interior flexible membranes attached to the shell to define right and left epicardial sacs adjacent to the ventricular heart myocardium and fluid pressure conduits connected into said sacs, the improvement which comprises:
   (a) separate pressure conduits entering the right and left sacs from the exterior of the device; and
   (b) means connected to each of said pressure conduits for generating documentation of the pressure conditions in said sacs.

2. The improvement set forth in claim 1 wherein said separate conduits enter the right and left sacs through the fluid pressure conduits.

3. The improvement set forth in claim 1 wherein said separate conduits enter the right and left sacs through the fluid pressure conduits, and said entry of said separate conduits into said pressure conduits is through sealed junctions substantially close to the shell.

4. The improvement set forth in claim 1 wherein said means connected to each of said pressure conduits include transducers for converting pressure values into substantially equivalent electrical signals.

5. The improvement set forth in claim 1 wherein said documentation generating means includes digital pressure readouts for the right and left sacs.

6. A method of documenting pressure conditions in a heart assist monitoring device consisting of
   (a) forming right and left epicardial sacs adjacent to the ventricular surfaces of a heart;
   (b) supplying a pressure medium to the sacs at a sufficient value to follow the heart functions; and
   (c) monitoring the pressure medium response and visually displaying the value of the pressure so monitored.

* * * * *